(12) United States Patent
Schwalbe et al.

(10) Patent No.: US 11,273,315 B2
(45) Date of Patent: Mar. 15, 2022

(54) METHOD AND DEVICE FOR DEFIBRILLATION (71) Applicant: WEINMANN EMERGENCY MEDICAL TECHNOLOGY GMBH + CO. KG, Hamburg (DE)

(72) Inventors: Billy Schwalbe, Hamburg (DE); Frank Herrmann, Barmstedt (DE)

(73) Assignee: WEINMANN EMERGENCY MEDICAL TECHNOLOGY GMBH + CO. KG, Hamburg (DE)

( * ) Notice: Subject to any disclaimer, the term of this patent is extended or adjusted under 35 U.S.C. 154(b) by 64 days.

(21) Appl. No.: 16/605,436

(22) PCT Filed: Apr. 26, 2018

(86) PCT No.: PCT/DE2018/000126
§ 371 (c)(1),
(2) Date: Oct. 15, 2019

(87) PCT Pub. No.: WO2018/196899
PCT Pub. Date: Nov. 1, 2018

(65) Prior Publication Data
US 2020/0121939 A1   Apr. 23, 2020

(30) Foreign Application Priority Data

Apr. 27, 2017 (DE) ..................... 10 2017 004 138.5
Jul. 13, 2017 (DE) ..................... 10 2017 006 868.2

(51) Int. Cl.
*A61N 1/39* (2006.01)
*A61N 1/362* (2006.01)

(52) U.S. Cl.
CPC ......... *A61N 1/3981* (2013.01); *A61N 1/3625* (2013.01); *A61N 1/3912* (2013.01)

(58) Field of Classification Search
CPC ... A61N 1/3981; A61N 1/3625; A61N 1/3912
See application file for complete search history.

(56) References Cited

U.S. PATENT DOCUMENTS

| | | | | |
|---|---|---|---|---|
| 5,397,946 A * | 3/1995 | Truong | ................. | G11C 5/143 327/74 |
| 6,493,580 B1 | 12/2002 | Cansell | | |
| 8,279,632 B2 | 10/2012 | Wohrle | | |
| 2004/0116967 A1 * | 6/2004 | DeGroot | .............. | A61N 1/3906 607/5 |
| 2006/0036287 A1 | 2/2006 | Bucher | | |

(Continued)

FOREIGN PATENT DOCUMENTS

| | | | |
|---|---|---|---|
| DE | 1006087 B | 4/1957 | |
| DE | 10064965 A1 * | 7/2001 | ............... A61N 1/39 |

(Continued)

*Primary Examiner* — Shirley X Jian
(74) *Attorney, Agent, or Firm* — Lucas & Mercanti, LLP; Klaus P. Stoffel (57) ABSTRACT

A method and a device for defibrillation. When a shock is generated, energy is transmitted from the low-voltage range to a high-voltage range, at least one current surge being generated in the low-voltage range, stepped up to the high-voltage range and guided to electrodes. An energy supply, power electronics and an energy storage device are used in the low-voltage range.

13 Claims, 10 Drawing Sheets

(56) References Cited

U.S. PATENT DOCUMENTS

| | | | | |
|---|---|---|---|---|
| 2007/0299474 A1* | 12/2007 | Brink | ............... | A61N 1/3904 607/7 |
| 2017/0244287 A1* | 8/2017 | Haaja | ............. | A61B 17/7216 |
| 2020/0321455 A1* | 10/2020 | Wood | ............. | H01L 29/7395 |

FOREIGN PATENT DOCUMENTS

| | | | | |
|---|---|---|---|---|
| DE | 10064965 A1 | 7/2001 | | |
| DE | 10254482 A1 | 6/2004 | | |
| DE | 60032039 T2 | 7/2007 | | |
| DE | 102008009859 A1 | 8/2009 | | |
| GB | 864362 A | 4/1961 | | |
| WO | WO-2014052347 A1 * | 4/2014 | ........... | A61N 1/3975 |

\* cited by examiner

METHOD AND DEVICE FOR DEFIBRILLATION

CROSS-REFERENCE TO RELATED APPLICATIONS

The present application is a 371 of International application PCT/DE2018/000126, filed Apr. 26, 2018, which claims priority of DE 10 2017 004 138.5, filed Apr. 27, 2017, and DE 10 2017 006 868.2, filed Jul. 13, 2017, the priority of these applications is hereby claimed and these applications are incorporated herein by reference.

BACKGROUND OF THE INVENTION

The invention relates to a method for defibrillation, in which energy is transformed from a low-voltage range into a high-voltage range and in which at least one current surge is generated and guided to electrodes.

The invention additionally relates to a device for defibrillation which has a low-voltage range and a high-voltage range and in which the low-voltage range is coupled to the high-voltage range and in which electrodes are arranged in the high-voltage range.

Methods and devices for defibrillation have long been part of the prior art. For example, corresponding methods and devices are described in DE 1006087 B and in GB 864362 A.

According to the prior art, in a defibrillator one or more capacitors are typically charged up to a high voltage of around 2,500 V. In the application of the defibrillator to a patient, by using a strong current surge delivered by the electrodes, the normal heart activity is then restored. The energy required for the current surge is stored in capacitors which, in view of the high voltage, have an appropriate breakdown strength and, consequently, are expensive and difficult to obtain.

Although defibrillators are also already known in which both a multi-voltage range and a high-voltage range is used, this functional principle has not yet gained wide acceptance, however. In a similar way to ignition coils for motor vehicles, in accordance with this principle a DC voltage pulse is generated in the low-voltage range, which is passed through a transformer and due to the abrupt current change, generates a high-voltage pulse in the high-voltage range.

In the defibrillators currently in use, the components used for their control are arranged in the high-voltage range so that only a few suppliers are available, which causes high production prices.

SUMMARY OF THE INVENTION

An object of the present invention, therefore, is to improve a method of the above-mentioned type in such a way that a reliable implementation of the method is supported with inexpensive components.

This object is achieved according to the invention by the fact that both an energy supply and a set of power electronics and an energy store are used in the low-voltage range.

A further object of the present invention is to construct a device of the above-mentioned type in such a way that high reliability is achieved with reduced manufacturing costs.

This object is achieved according to the invention by the fact that both an energy supply and a set of power electronics and an energy store are arranged in the low-voltage range. This means that electronic components with a better availability and lower costs can be more frequently used.

Due to the method according to the invention and the device according to the invention, it is possible to arrange both an energy supply and a set of power electronics and an energy storage system in a low-voltage range, advantageously in a maximum voltage range of approximately 40 V to 400 V, particularly advantageously in a range up to approximately 150 V. As an energy supply, for example, a battery or a mains power supply is used.

The lower the maximum voltage in the low-voltage range, the cheaper the required electronic components that can have a correspondingly lower voltage breakdown strength tend to be.

In the low-voltage range of a device according to the invention for defibrillation, in addition to the energy store, the power electronics and the energy supply, which is implemented as a mains power supply or a battery or a rechargeable battery, for example, at least a charge regulator and a processor are advantageously arranged.

In a preferred embodiment of the invention the charge regulator is used to charge the energy store, so that it has at least the minimum energy needed for producing an electric shock.

In an advantageous embodiment of the invention the processor is used to control the relevant functions of the device according to the invention for defibrillation and is used for the implementation of the method according to the invention for defibrillation.

In an advantageous embodiment of the invention, the energy store delivers the energy at the moment of the shock to be generated, and using a voltage converter this is transformed into a high voltage by additionally using a translator. The transformed high-voltage can then be delivered to a patient via electrodes.

In the high-voltage region behind the translator (secondary side), due to the design according to the invention only relatively few components need to be arranged. These are, for example, the electronic components required for a phase controller and a measuring device for performing an optional current and/or voltage measurement.

According to the invention the result achieved, in particular, is that it allows at least part of the power electronics and the control devices for current, voltage and phase to be arranged in the low-voltage range, so that low-cost standard components can be used.

The power control can be implemented in a very broad power range. This covers a range of functions from a simple pacemaker function up to generating high-power shocks.

In particular, it is possible to implement the energy store in a preferred embodiment of the invention with inexpensive, low-voltage components, such as capacitors and/or super-capacitors and/or (high-power) rechargeable batteries and/or standard batteries.

Due to an advantageously designed energy storage according to the invention, it is also possible, in particular, to achieve immediate operational readiness of the device for defibrillation without a lead time to perform charging. For this purpose it is necessary to design the energy store in such a way that, even in an off state of the device for defibrillation, the energy store obtains a minimum energy needed for realizing a shock or cardiac pacemaker function. In addition, several shocks can be generated at short time intervals relative to each other.

The actual high-voltage generation takes place immediately before the delivery of the shock. This increases the safety of the system.

For the translator, the basic principle of a transformer with correspondingly adapted windings can be used. For implementing the phase control, different design variants are possible. This can be carried out, for example, by using diodes, thyristors, triacs or transistors. If appropriate, a multi-level structure and/or a structure with a parallel connection of a plurality of paths can be implemented.

An embodiment according to the invention of a device for defibrillation with a design of the translator having a plurality of secondary windings or the use of a plurality of translators connected in series can generate additional benefits, since the use of a smaller high-voltage per winding means that standard electronics, in the sense of less expensive electronic components, are more likely to be usable on the high-voltage side due to a reduction in the requirement for voltage breakdown strength. Particularly advantageously, the translator is designed according to the invention on the primary side with at least two parallel-connected windings and on the secondary side with at least two series-connected windings.

In a preferred embodiment of the invention, therefore, this is characterized in that at least two of the primary and/or secondary windings of the translators are combined by a series and/or a parallel circuit.

If, for example, high voltages of only about 800 V to 1200 V per winding are generated, a wide range of electronic components, such as semiconductor devices, are available for use. By cascading these high voltages, the necessary voltage for defibrillation can be generated. The separate windings can also be used to ensure that, for example, in the case of the pacemaker function only one winding tap is used for power generation, since in this case a significantly lower voltage is required compared to the shock function.

In a particularly advantageous embodiment of the invention the voltage converter for generating the high voltage is implemented in conjunction with the translator as a resonance voltage converter, so that higher efficiencies can be achieved in the high-voltage generation. The switching losses can be reduced by switching at a zero-crossing of the applied voltage or a zero-crossing of the current flowing. In the resonance case a current source behavior of the converter is implemented. Furthermore, an additional voltage gain is achieved by the resonance reinforcement.

In an advantageous embodiment of the invention, in addition to the already mentioned cost reduction, the arrangement of the essential control components in the low-voltage range also supports a reduction in the size of the electronic components used and in the required minimum distances between the voltage-carrying components for a safe isolation, allowing more compact devices to be implemented. In addition, an arrangement according to the invention of the components enables a simpler and more cost-effective layout of the circuit boards.

On the high-voltage side, a phase controller, or the power electronic components associated with a phase controller, is/are advantageously arranged between the translator and the output of the device for defibrillation given by the two electrodes (apex and sternum electrode). With this phase controller, from the DC voltage output signal of the voltage converter which is generated from the AC voltage signal on the secondary side of the translator using a rectifier, a biphasic pulse can be generated.

According to the invention the phase controller is advantageously implemented as a controlled rectifier. For example, the controlled rectifier is implemented as an H-bridge or a cascaded H-bridge. In this case, the control of the transistors is advantageously isolated from the direction of the primary side. Instead of the diodes an embodiment with thyristors is also envisaged, which can be triggered, for example, via a small high-voltage capacitor. An embodiment using triacs is also envisaged.

A method according to the invention for defibrillation comprises at least the following steps:
a. providing the energy required for the current surge in the high-voltage range by means of an energy store in the low-voltage range,
b. controlling a voltage converter having at least one translator by means of a processor arranged in the low-voltage range, so that on the high-voltage side a high-voltage signal or a current surge is generated,
c. controlling the phase of the high-voltage signal or current surge, so that either a monophasic or a biphasic high-voltage signal, or a monophasic or biphasic current surge is generated,
d. delivering the high-voltage signal or current surge via the electrodes to a patient for implementing a shock function or a pacemaker function.

BRIEF DESCRIPTION OF THE DRAWING

Different exemplary embodiments and designs of the invention are shown in the following figures. Shown are.

DETAILED DESCRIPTION OF THE INVENTION

Figure 1:
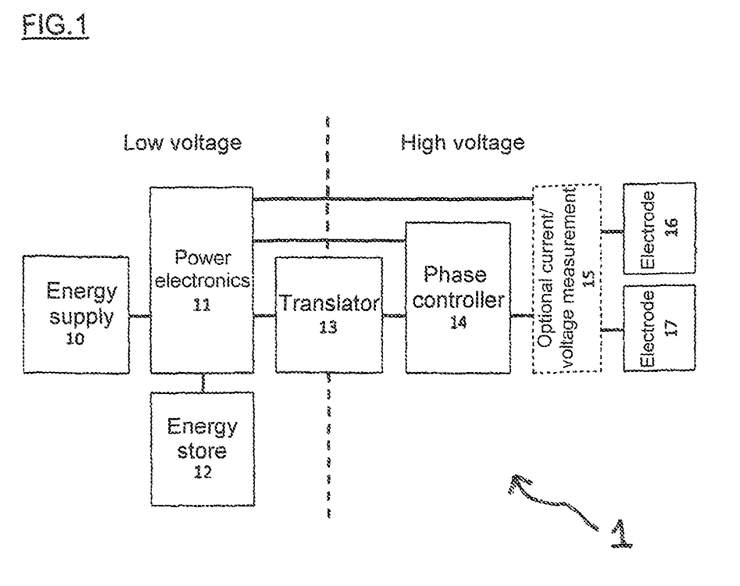
FIG. 1: a block circuit diagram as a schematic representation of the physical structure of a device according to the invention for defibrillation.

FIG. 1 shows a block circuit diagram of a device according to the invention for defibrillation (1), and in particular illustrates the coupling of the low-voltage region to the high-voltage region by means of a translator (13). In the low-voltage region a power supply (10) and an energy store (12) are arranged together with the power electronics (11).

In the high-voltage region the phase controller (14) and two electrodes (16, 17) are arranged. Optionally, a device for current and/or voltage measurement (15) can be arranged in the high-voltage range.

Figure 2:
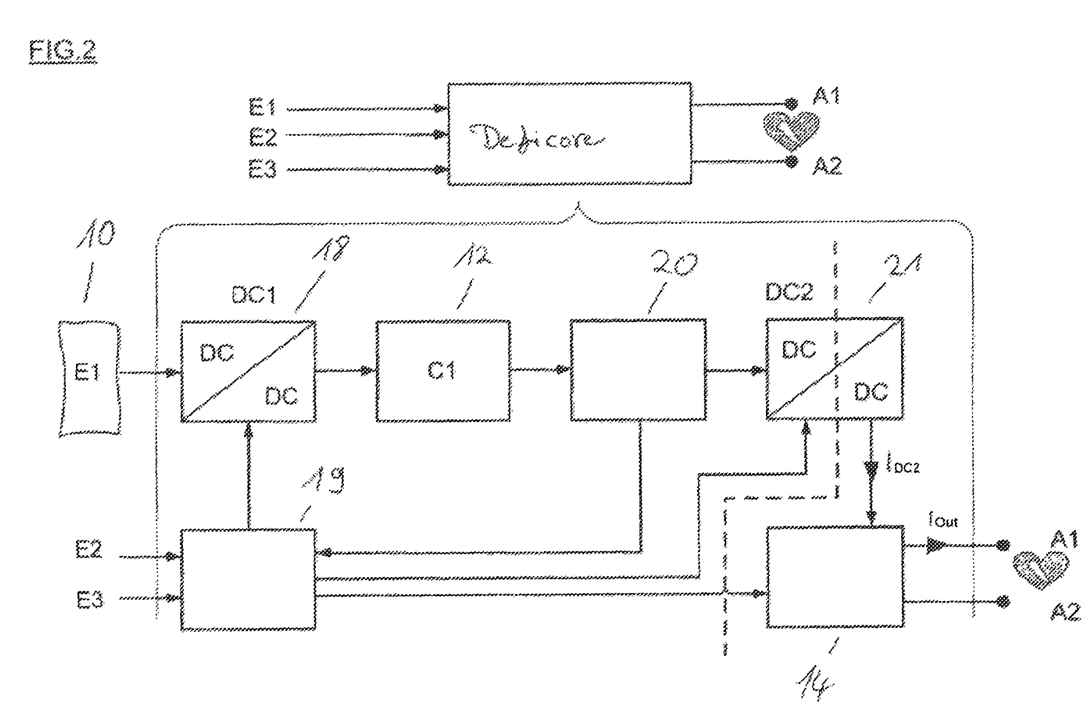
FIG. 2: a detailed block diagram to illustrate a design variant of a device according to the invention for defibrillation.

FIG. 2 shows the layout of the overall system of an embodiment according to the invention of a device for defibrillation (1) in an overview drawing. Illustrated in particular is the electronic part of the apparatus for defibrillation (1) with which the defibrillation pulse can be generated.

The input signals E1, E2 and E3 of this so-called Deficore are provided by the energy supply (E1), which in an advantageous embodiment of the invention has a voltage of approximately 12 V at an available power of approximately 50 W to 100 W, the signal for activating a shock (E2), and a configuration signal (E3), which can be transmitted via an I2C interface, for example.

With the Deficore the defibrillation pulse can be delivered to a patient via the electrodes of the patient connector. The patient connector comprises the terminals apex (A1) and sternum (A2).

Using a device according to the invention for defibrillation (1), in an advantageous embodiment the energy store (12) can be used to deliver an energy of approximately 200 Ws and to generate a high-voltage pulse of approximately 2,000 V. The energy that can be stored using the energy store (12) is composed of at least the deliverable energy and the energy needed to compensate for the losses occurring within the device according to the invention for defibrillation.

In particular, it is envisaged to generate a biphasic shock with a length of roughly 10 ms. The intensity of the shock current is typically up to 20 Amperes.

According to one embodiment of the device according to the invention for defibrillation (1) and/or a method according to the invention for defibrillation, a user can choose whether the shock current is to be generated in a biphasic or monophasic form, and the shock length that should be generated.

In accordance with the diagrams in FIG. 3 the function of generating a biphasic shock will be explained again in detail by means of an example.

Figures 3, 31:
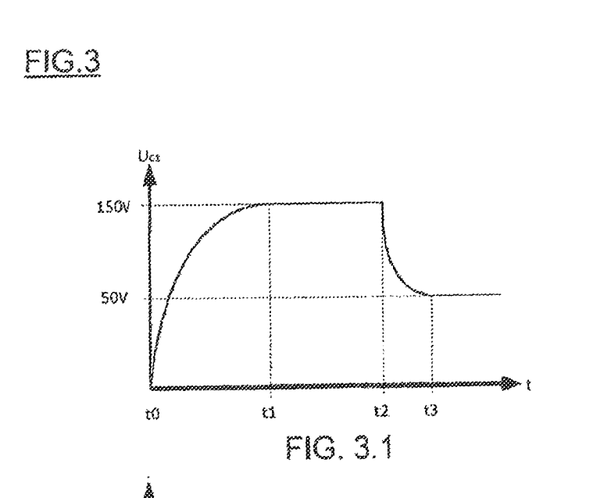
FIG. 3: timing diagrams to illustrate the functional sequence.
Figure 32:
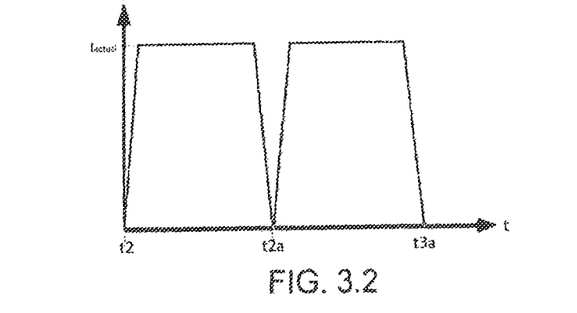
Figure 33:
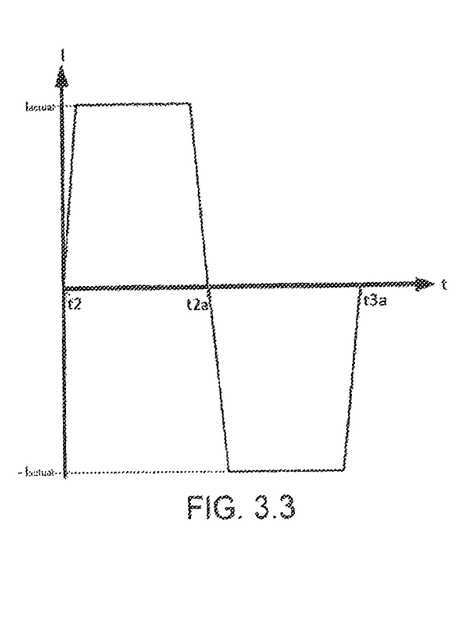

FIG. 3.1 shows the voltage waveform UC1 on the capacitor C1 as a function of time t, FIG. 3.2 shows the current waveform $I_{DC2}$ at the output of the voltage converter DC2 (21) as a function of time t and FIG. 3.3 shows the current waveform $I_{OUT}$ at the output of the device for the defibrillation (1) as a function of time t.

In the case of a function that starts at time t0 all voltages are initially set to 0 V and all currents to 0 Amperes. On switching on the supply voltage of the device for defibrillation (1), the charge regulator (18) is started and begins to charge the energy store (12) in the form of capacitor C1 with the injected current.

At time t1 the energy store (12) is fully charged and the voltage level on the capacitor C1 is approximately 150 V. The required voltage level on the energy store (12) depends on the energy to be delivered. The charging of the energy store (12) is carried out adaptively and typically to a voltage of up to approximately 200 V.

In a further step, the processor (19) shown in FIG. 2 then triggers the shock at time t2 and a pulse-width modulation is applied to the voltage converter DC2 (21). In addition, the phase controller (14) implemented as an H-bridge is then enabled.

In a further method step, the processor (19) regulates the current of the shock by modulation of the pulse widths and/or the frequency and/or the phase angle of the control signals for the power electronics. To do so, via the voltage converter DC2 (21), the capacitor voltage is transformed by means of the translator (13) up to the required potential of up to approximately 2,500 V on the high-voltage side. At the output of DC2 and at the output of the H-bridge, a current $I_{DC2}$ and $I_{OUT}$ with a current intensity corresponding to $I_{Actual}$ are produced.

In a subsequent step at time t2a, the current $I_{DC2}$ at the output of the DC2 is briefly reduced to 0 Amperes, causing the H-bridge to switch over in order to generate a biphasic pulse.

The currents $I_{DC2}$ and $I_{OUT}$ then increase back up to the current $I_{Actual}$ before they are reduced to 0 Amperes again at time t3a, and the generation of a shock pulse is completed.

During the generation of the shock with the current waveform $I_{OUT}$ the energy store (12) discharges and the voltage across the capacitor C1 falls according to FIG. 3.1 between the times t2 and t3 to a residual voltage of roughly 50 V. The residual voltage depends on the required shock energy and the dimensions of the translator (13).

In accordance with a further method step, the current values and voltage values required for the control scheme are measured in front of the voltage converter DC2 (21). In general, these measurements can also take place behind the voltage converter DC2 (21). In the second case, however, a potential isolation is applied between the processor (19) and the measuring point (20).

Figure 4:
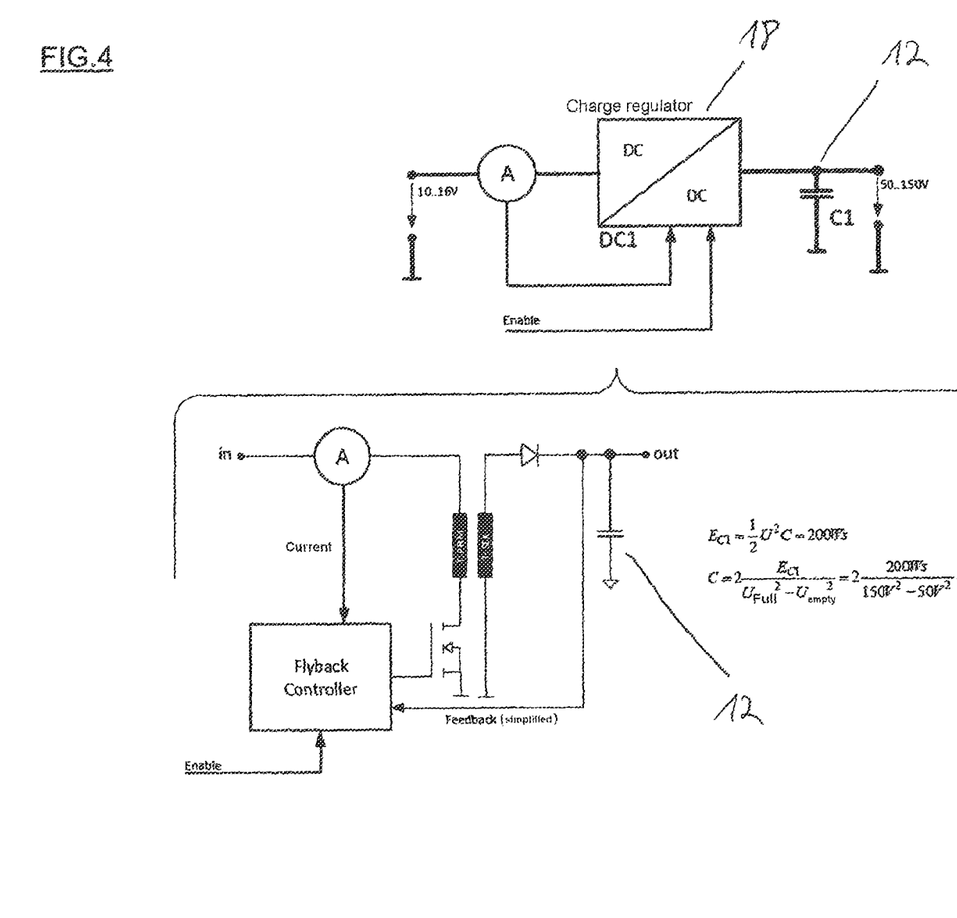
FIG. 4: a schematic representation of the structure of the charge regulator circuit of the storage capacitor.

The drawing of FIG. 4 illustrates details of the charge regulator (18) and the energy store implemented as a capacitor C1 (12).

In the region of the capacitor C1 the energy required for the shock plus the energy required to compensate for the losses is stored, and the charge regulator (18), implemented as a DC-DC converter, charges the capacitor C1. During the charging of the capacitor C1 the input current is preferably limited.

To implement the charge regulator (18) a flyback topology is preferably chosen, in order to generate a high voltage difference between input and output.

For the capacitor C1 a commercially available electrolytic capacitor can be used, for example, but other types of capacitor such as super-capacitors or ceramic capacitors are also conceivable.

In the case of an example energy of 200 Ws to be stored in the capacitor C1, at a specified applied voltage of approximately 150 V in the fully charged condition and a specified applied voltage of approximately 50 V after the discharge by the energy output in generating a shock, a capacitor C1 with a capacity of approximately 10 mF is required. The corresponding formulae are shown in FIG. 4 without taking into account the losses occurring.

Figure 5:
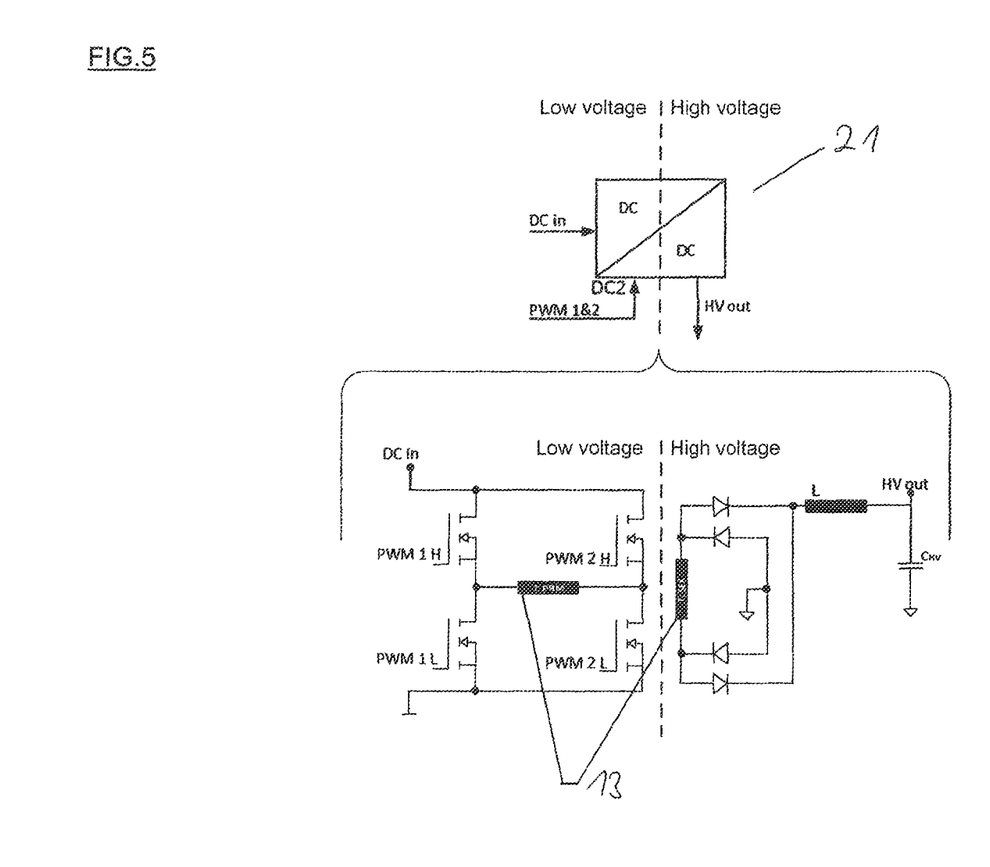
FIG. 5: a schematic representation of the circuit design of a push-pull converter and a transformer for translating the shock energy from the low-voltage range into the high-voltage range.

In the drawing in FIG. 5, further details of the voltage converter DC2 (21) and the translator (13) are illustrated.

The voltage converter DC2 (21) transfers the shock energy from the low-voltage side to the high-voltage side using the transformer (13). The voltage converter DC2 (21) can be implemented as a push-pull converter, for example.

On the low-voltage side of the voltage converter DC2 (21) a full-bridge circuit with power transistors is implemented. The power transistors are each driven using a pulse-width modulated signal (PWM 1 H/L, PWM 2 H/L), so that the direction of the current flow through the at least one primary-side winding of the at least one transformer (13) can be controlled.

On the secondary side of the transformer (13) a bridge rectifier implemented with diodes, which is followed by an L-C filter, is connected downstream of the winding. At the terminal HV out, therefore, a DC voltage signal in the high-voltage range can be tapped off.

A power of, for example, 20 kW for a period of 10 ms is output to deliver an energy of 200 Ws.

In a preferred embodiment of the invention the voltage converter DC2 (21) can be controlled directly by the processor (19) or by the processor (19) in conjunction with gate drivers.

The translator (13) designed as a step-up transformer can be implemented, for example, in planar technology. In addition, it is also conceivable to connect a plurality of transformers in parallel with each other, and thus to implement the voltage converter DC2 (21) as a multi-parallel push-pull converter. It is also possible to use transformers with multiple secondary windings and/or multiple transformers with one or more secondary windings in one embodiment according to the invention of a device for defibrillation (1).

According to the design variant shown in FIG. 5, a typical high-voltage range from approximately 2,000 V to 2,500 V is implemented. Here, also, the high voltage is preferably generated exclusively during the delivery of the shock. For a power output of typically 200 Ws and a patient resistance of 25 to 175 Ohms (typically 50 Ohms), a voltage of 750 V to 2 kV is required.

Figure 6:
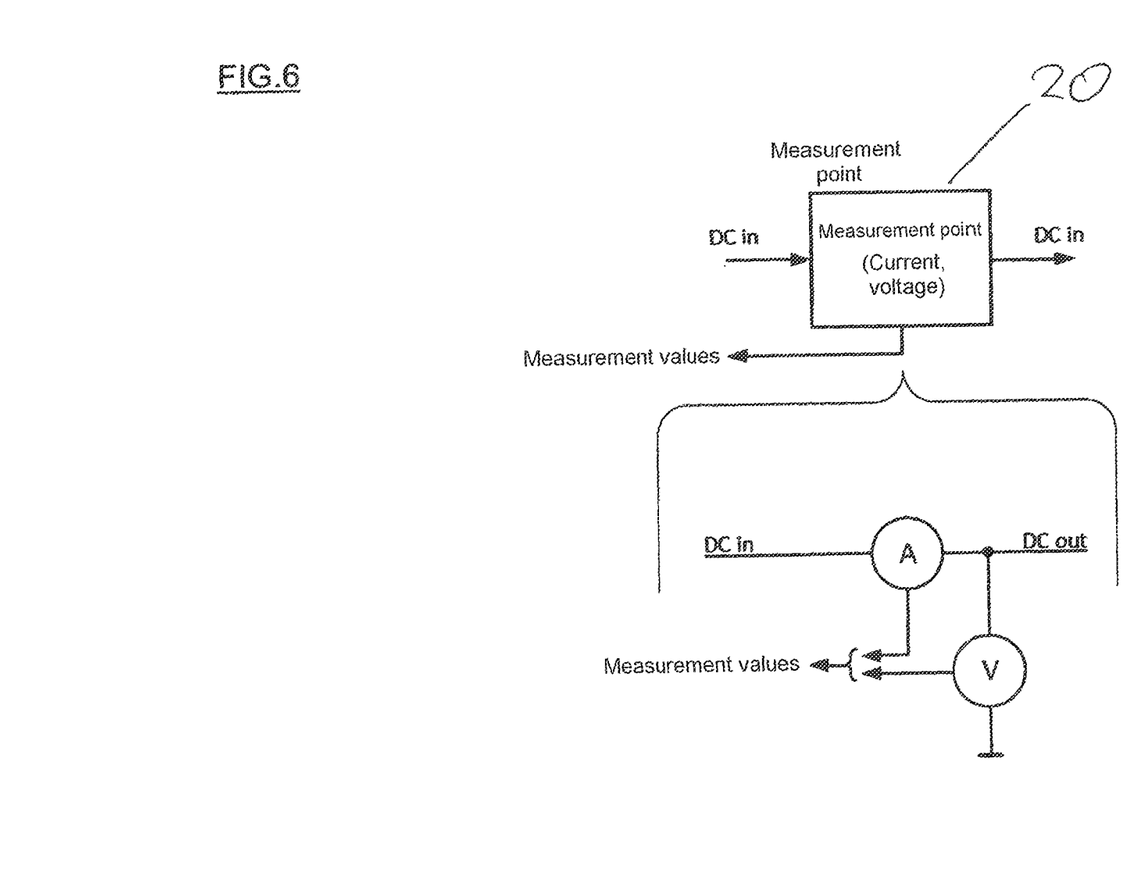
FIG. 6: a schematic representation of a measurement point for current and voltage.

In the drawing of FIG. 6, further details of the current and voltage measurement are illustrated.

The discharge current from the capacitors can be measured and the corresponding value provided for the regulation.

The measurement can be carried out continuously or on a sampled basis. A typical sampling frequency is in the range of 20 to 40 kHz. This equates to approximately 200 to 400 measurements per shock duration.

According to a preferred embodiment variant, the current and voltage are measured behind the voltage converter DC2 (21) and in front of the H-bridge on the high-voltage side.

Figure 7:
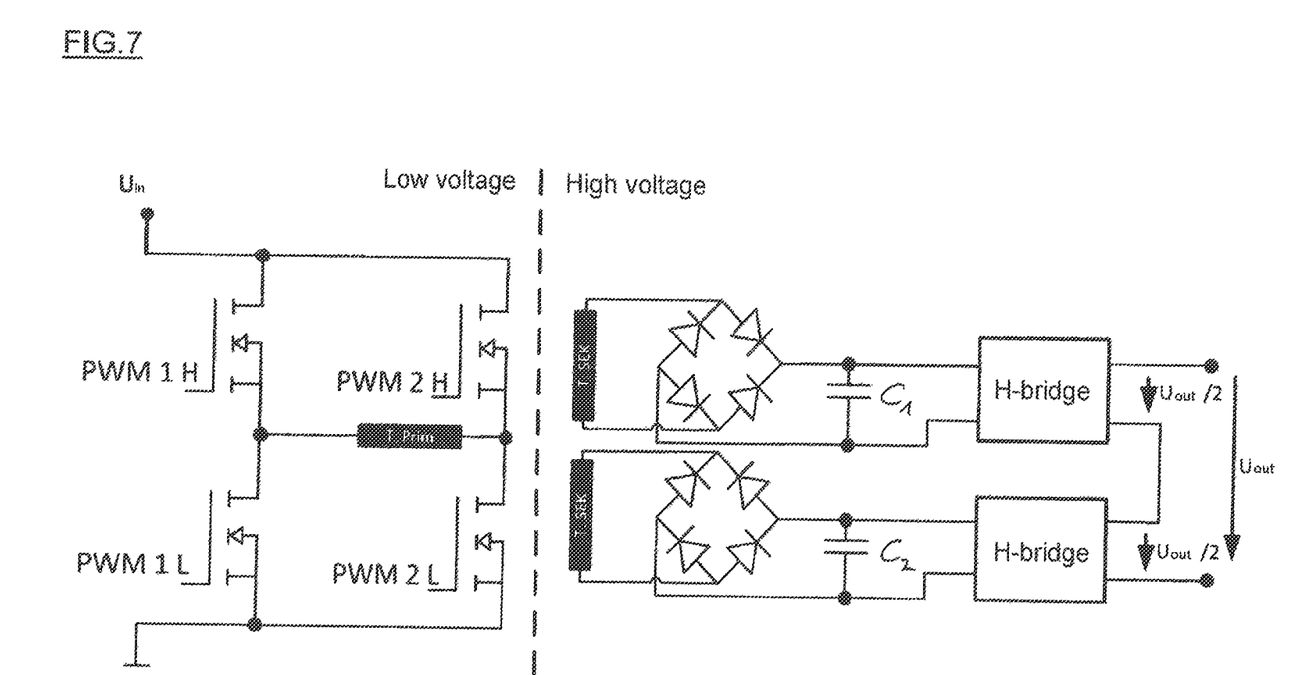
FIG. 7: a circuit diagram of an embodiment according to the invention of a multi-level translator.

FIG. 7 shows a schematic representation of a circuit diagram of an exemplary multi-level design of the translator (13) according to the invention followed by a rectifier circuit. The voltage applied on the primary side Uin (input voltage of the H-bridge of the inverter), can be transformed via the translator (13) into a high-voltage range and converted using rectifiers into the output voltage Uout. On the primary side the translator (13) has a winding (T: Prim), while on the secondary side two windings (T: SEK) connected in series are arranged. The translator (13) has an exemplary winding ratio of 1:8.

A bridge rectifier implemented using diodes, and a capacitor (C1, C2) and an H-bridge are connected downstream of each of the secondary-side windings (T: SEK) of the translator (13). Across each of the series-connected secondary-side circuit branches, therefore, only half of the output voltage Uout is dropped. According to the invention, the semiconductors and capacitors on the secondary side therefore require only half the voltage breakdown strength.

Figures 8, 81:
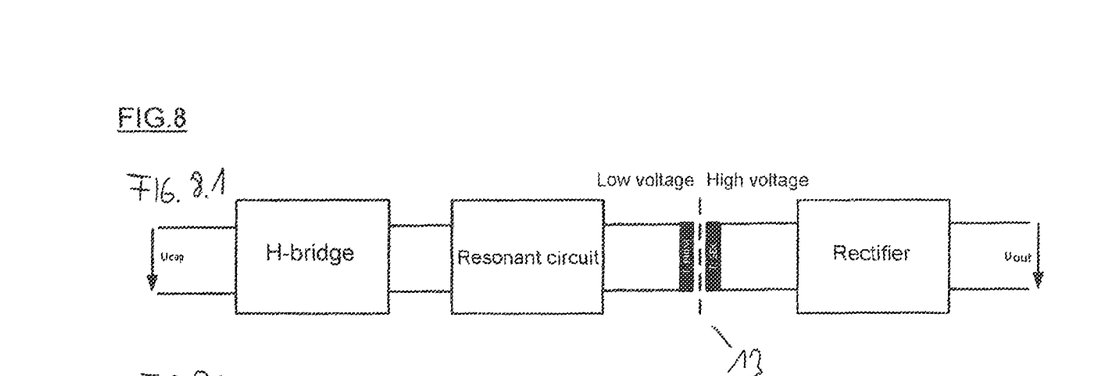
FIG. 8: three schematic block circuit diagrams for various topologies according to the invention of a resonance converter.

FIG. 8 shows three topologies according to the invention of a resonance converter for transforming the shock energy from the low-voltage range into the high-voltage range.

FIG. 8.1 shows an arrangement of the resonant circuit between the H-bridge of the inverter and the primary side of the translator (13) in the low-voltage range.

Figure 82:
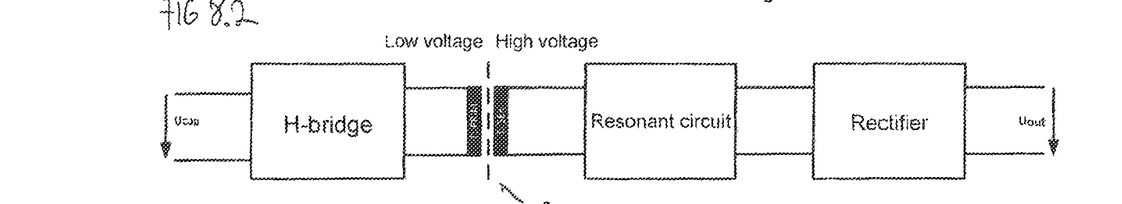

FIG. 8.2 shows an arrangement of the resonant circuit on the secondary side of the translator (13) before the rectifier.

Figure 83:
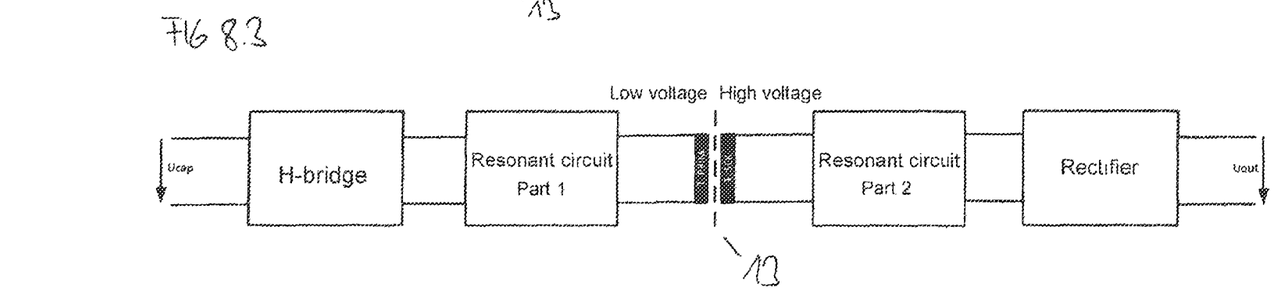

FIG. 8.3 shows a combined arrangement of the resonant circuit on the primary and secondary side of the translator (13).

Figure 9:
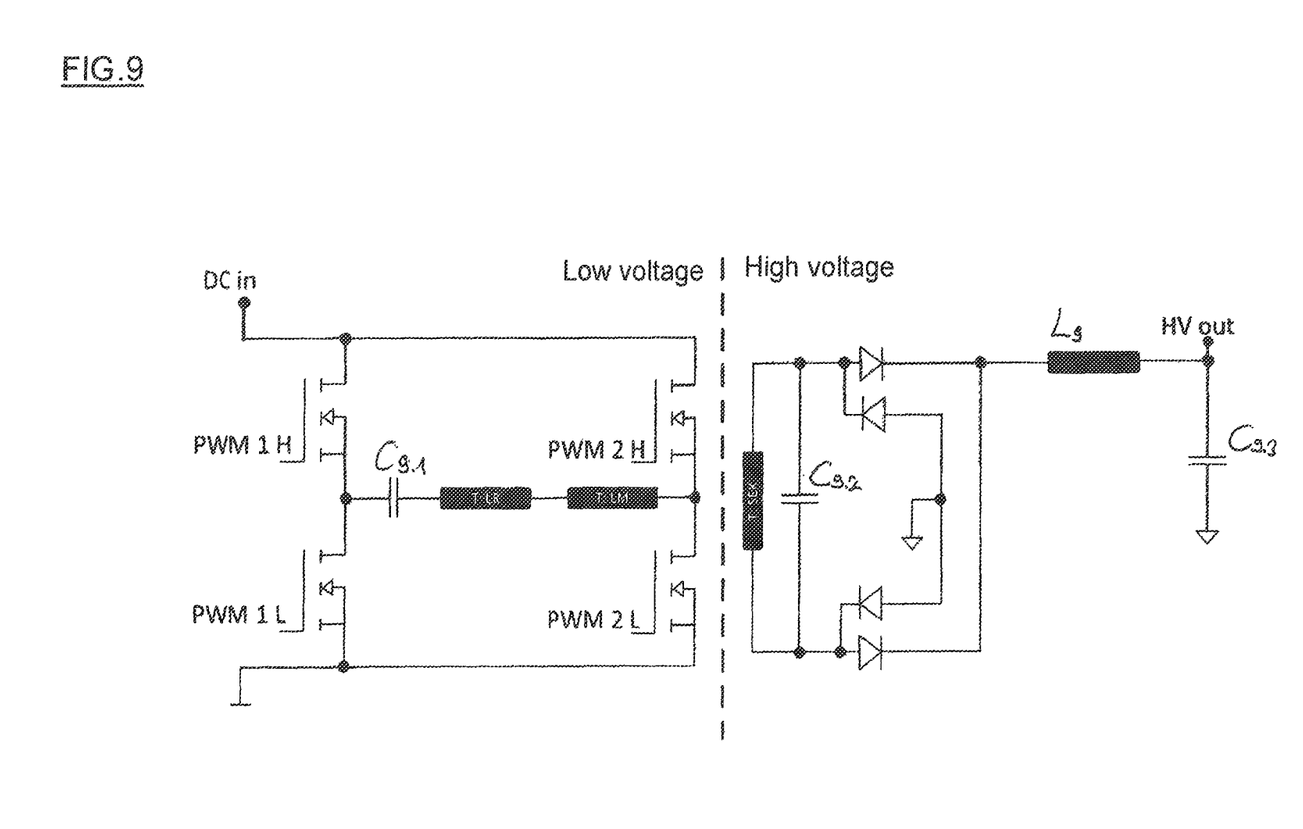
FIG. 9: a circuit diagram of a resonant circuit according to the invention with translator and rectifier.

FIG. 9 shows a circuit diagram of a resonant circuit according to the invention with a transformer. The resonant circuit is implemented as a combined topology on the primary and secondary side of the translator (13).

The voltage DCin (input voltage of the inverter in the low-voltage range) can be converted into the output voltage HVout using the components shown.

The relevant components for setting the desired operating point (resonant frequency) of the resonant circuit or the resonant converter are the stray inductance T: LR of the transformer or translator (13), and the secondary-side capacitor $C_{9.2}$ (resonance capacitor). In an advantageous embodiment of the device according to the invention the values of the primary magnetizing inductance T: LM of the translator (13) and of the capacitor $C_{9.1}$, which is used for DC suppression in the translator (13), are dimensioned in such a way that the desired operating point of the resonant circuit is not changed. This is usually solved by positioning an additionally resulting resonance frequency as far away as possible from the frequency of the operating point.

The rectifier implemented using diodes has a filter connected downstream, which is provided by the components $L_9$ and $C_{9.3}$.

Figure 10:
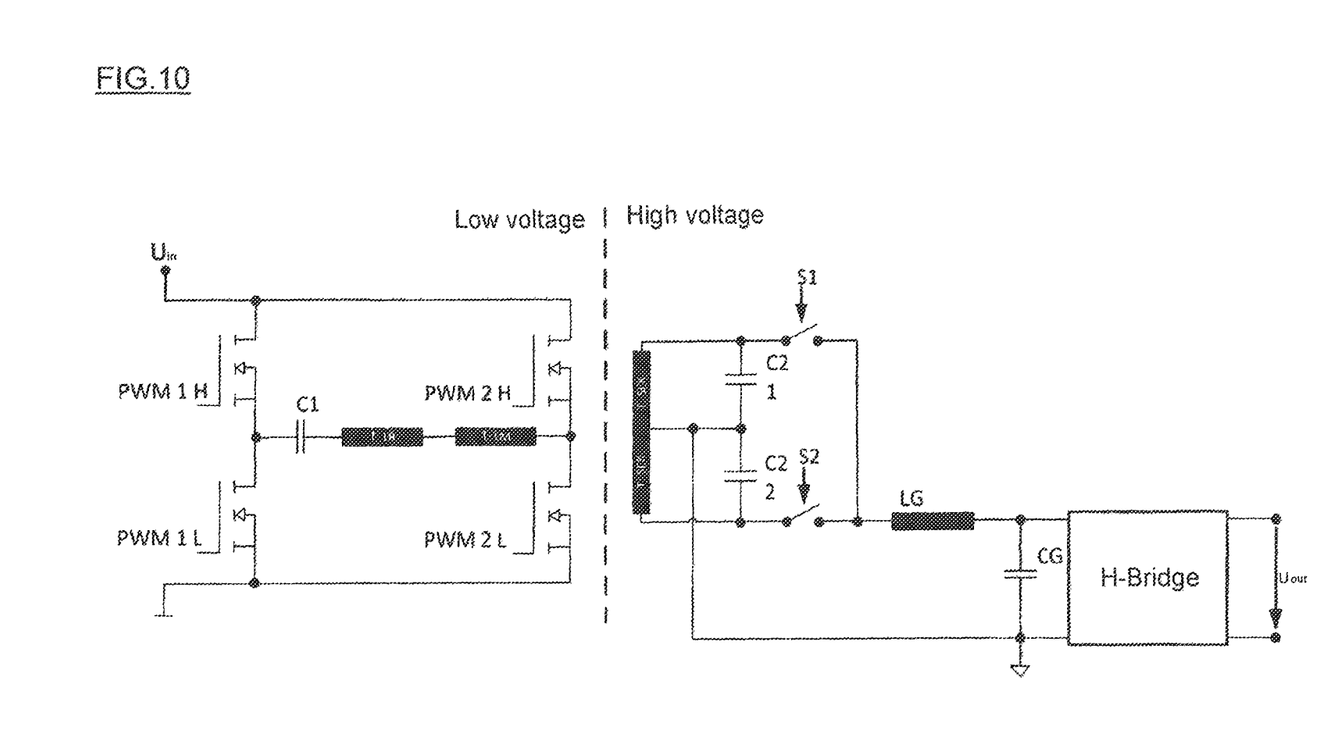
FIG. 10: a circuit diagram of a synchronous rectifier based on the example of a translator with a resonant circuit.

FIG. 10 shows a circuit diagram of a switchable rectifier, implemented as a synchronous rectifier, based on the example of a translator (13) with a resonant circuit.

The input voltage $U_{IN}$ can be converted into the output voltage $U_{OUT}$ using the components shown.

The secondary-side rectifier has the switches S1 and S2, wherein the rectifier function can be implemented by means of an active and synchronous control of the switches S1 and S2.

Depending on the switching sequence of S1 and S2, a positive or negative voltage $U_{OUT}$ can be generated. The switches S1 and S2 must be embodied as semiconductors that can be closed and opened bidirectionally.

The invention claimed is:

1. A device for defibrillation, which has a low-voltage side with a low-voltage range of 40 V to 400 V and a high-voltage side with a high-voltage range of 2000 V to 2500 V, comprising: at least one translator that couples the low-voltage range to the high-voltage, range, the translator having a primary part and a secondary part; electrodes arranged in the high-voltage range; a power supply, a set of power electronics, and an energy store arranged in the low-voltage range, the energy store being configured to provide an amount of energy of about 200 WS to generate a high voltage peak of about 2000 V; and a voltage converter for converting a current surge from the low-voltage range into the high-voltage range, wherein the voltage converter is a resonance converter, wherein the translator is part of the voltage converter.

2. The device according to claim 1, wherein the device is operative to generate a high voltage temporarily and on demand.

3. The device according to claim 1, further comprising a processor arranged on the low-voltage side to control the device.

4. The device according to claim 1, wherein the energy store includes at least one of the group consisting of a capacitor, a super-capacitor, an accumulator, and a battery.

5. The device according to claim 1, wherein the energy store is configured to store energy so that the device is able to generate a shock instantaneously after being switched on.

6. The device according to claim 1, wherein the at least one translator has at least one primary and/or secondary winding.

7. The device according to claim 6, wherein at least two primary and/or secondary windings of the at least one translator are combined by a series and/or a parallel circuit.

8. The device according to claim 7, wherein the secondary windings of the at least one translator are interconnected in series so that electronic components with a maximum voltage breakdown strength specified in a range from about 500 V to about 1500 V are useable on the high-voltage side.

9. The device according to claim 1, wherein the device is configured to generate both a monophasic and a biphasic output pulse.

10. The device according to claim 1, further comprising an element to measure a current and/or voltage on the primary part or the secondary part of the at least one transfer element.

11. A method for defibrillation, comprising the steps of: translating energy from a low-voltage range into a high-voltage range; and, in the high-voltage range, generating at least one current surge and guiding the current surge to electrodes, wherein the method includes using a device according to claim 1 to carry out the steps.

12. The method according to claim 11, including controlling the generation of the current surge in the high-voltage range with a processor arranged in the low-voltage range.

13. The method according to claim 11, including the steps of:
a. providing energy required for the current surge in the high-voltage range by an energy store in the low-voltage range;
b. controlling a voltage converter having at least one translator by a processor arranged in the low-voltage range so that a high-voltage signal or the current surge is generated on the high-voltage side;
c. controlling a phase of the high-voltage signal or current surge so that either a monophasic or a biphasic high-voltage signal or a monophasic or biphasic current surge is generated; and
d. delivering the high-voltage signal or current surge via the electrodes to a patient for implementing a shock function or a pacemaker function.

* * * * *